(12) United States Patent
Blair-Pattison et al.

(10) Patent No.: US 10,290,234 B2
(45) Date of Patent: May 14, 2019

(54) SIMULATED BONE MATERIALS AND METHODS OF MAKING SAME

(71) Applicant: AMMOLITE BIOMODELS INC., Calgary (CA)

(72) Inventors: Aubrey Jeanine Blair-Pattison, Calgary (CA); Carolyn Ruth Anglin, Calgary (CA); Richard Wei-Chi Hu, Calgary (CA); Christine Renee Jansen, Calgary (CA)

(73) Assignee: Ammolite Biomodels Inc., Calgary, Alberta (CA)

( * ) Notice: Subject to any disclaimer, the term of this patent is extended or adjusted under 35 U.S.C. 154(b) by 27 days.

(21) Appl. No.: 15/544,412

(22) PCT Filed: Jan. 18, 2016

(86) PCT No.: PCT/CA2016/050037
§ 371 (c)(1),
(2) Date: Jul. 18, 2017

(87) PCT Pub. No.: WO2016/115625
PCT Pub. Date: Jul. 28, 2016

(65) Prior Publication Data
US 2018/0005548 A1    Jan. 4, 2018

Related U.S. Application Data

(60) Provisional application No. 62/105,102, filed on Jan. 19, 2015.

(51) Int. Cl.
*A61F 2/28* (2006.01)
*A61L 27/56* (2006.01)
(Continued)

(52) U.S. Cl.
CPC ............... *G09B 23/30* (2013.01); *A61F 2/28* (2013.01); *A61L 27/18* (2013.01); *A61L 27/20* (2013.01); *A61L 27/40* (2013.01); *G09B 23/34* (2013.01); *A61F 2/44* (2013.01); *A61L 27/56* (2013.01); *A61L 2430/02* (2013.01)

(58) Field of Classification Search
None
See application file for complete search history.

(56) References Cited

U.S. PATENT DOCUMENTS 4,230,455 A * 10/1980 Hidaka ............... A61C 8/0012
433/202.1
4,904,257 A * 2/1990 Mori ...................... A61F 2/28
106/161.1

(Continued)

*Primary Examiner* — Thomas Sweet
*Assistant Examiner* — Javier G Blanco
(74) *Attorney, Agent, or Firm* — Gowling WLG (Canada) LLP

(57) ABSTRACT

An artificial bone is provided comprising an inner core made from a porous material, the porous material comprising at least one fiber component having fibers, a liquid and a binder, and an outer layer comprising at least one fiber component having fibers, a liquid and a binder, wherein the ratio of the at least one fiber component having fibers to liquid to binder of the inner core is different from the ratio of the at least one fiber component having fibers to liquid to binder of the outer layer.

8 Claims, 2 Drawing Sheets

(51) Int. Cl.
    *G09B 23/30*   (2006.01)
    *A61L 27/20*   (2006.01)
    *A61L 27/40*   (2006.01)
    *G09B 23/34*   (2006.01)
    *A61L 27/18*   (2006.01)
    *A61F 2/44*    (2006.01)

(56) References Cited

U.S. PATENT DOCUMENTS

| | | | | |
|---|---|---|---|---|
| 5,425,769 | A * | 6/1995 | Snyders, Jr. | A61F 2/28 |
| | | | | 623/23.61 |
| 2002/0155137 | A1* | 10/2002 | Lee | A61F 2/28 |
| | | | | 424/400 |
| 2003/0228288 | A1* | 12/2003 | Scarborough | A61K 35/32 |
| | | | | 424/93.7 |
| 2007/0190083 | A1* | 8/2007 | Scifert | A61L 24/0084 |
| | | | | 424/400 |
| 2009/0254194 | A1* | 10/2009 | Peters | A61L 27/46 |
| | | | | 623/23.61 |
| 2011/0206828 | A1* | 8/2011 | Liu | A61F 2/28 |
| | | | | 427/2.24 |
| 2012/0245703 | A1* | 9/2012 | Meredith | A61F 2/28 |
| | | | | 623/23.51 |
| 2014/0134258 | A1* | 5/2014 | Tampieri | A61L 27/10 |
| | | | | 424/491 |
| 2014/0220142 | A1* | 8/2014 | Song | A61F 2/28 |
| | | | | 424/489 |
| 2015/0165092 | A1* | 6/2015 | Kaplan | A61L 27/56 |
| | | | | 424/130.1 |

* cited by examiner

SIMULATED BONE MATERIALS AND METHODS OF MAKING SAME

FIELD OF THE INVENTION

The present invention is in the field of simulated bone materials and the production thereof and the manufacture of artificial bones for use in training on bone-related procedures.

BACKGROUND OF THE INVENTION

Current training practices for bone-related procedures (e.g., orthopaedic surgery, dentistry, veterinary medicine etc.) in human and animal health, where bone is probed, drilled, cut, sawed, burred, or punctured or is manipulated to adjust or repair deformity or damage, relies almost exclusively on a master-apprentice model. In this approach, the experienced clinician performs the procedure with the apprentice observing, and over time the apprentice is allowed to engage in a progressively more advanced manner with the procedure. For the procedures discussed herein this is usually on living people or animals. While there are alternative approaches that rely upon various levels of simulation, they each have distinct disadvantages in the context of these procedures that rely heavily on accurate tactile and visual feedback; as a result, training continues to rely upon the apprentice approach during live procedures. This approach is high risk since any mistake by the apprentice can be catastrophic for the person or animal undergoing the procedure; there is limited operating room time under which such apprenticeship can be offered; and there is no mechanism that allows the trainee to repeat procedures multiple times in succession, experiencing how the procedure feels when performed both correctly and incorrectly, without negative consequences.

In terms of alternative approaches, the use of cadaveric specimens provides a realistic experience of the tactile feedback since it uses real bone, although almost all are from older people, which may not represent the typical patient population. The visual cues are also reasonably accurate for many of the procedures since the covering tissues need to be addressed in the similar way they would be in an actual procedure (the reduction of blood and other living related fluids notwithstanding). However, the challenge with cadaveric approaches is they are in limited supply, and expensive, so the expectation is that the trainee performs the procedure correctly, and only limited opportunities are provided. Thus the cadaveric approach does not lend itself to a training pedagogy that allows for repeated attempts at the same procedure in the same session and in a manner that allows for experiencing the tactile feedback of both correct and incorrect procedures. The high cost and low availability of cadaveric specimens is a trend in both the human case (where donation rates are low) and the animal case (where growing concerns over the treatment of animals has substantially reduced the availability of cadaveric specimens).

Current simulated bones are designed to look like bone but do not reproduce the tactile and structural properties of bone. These simulated bone materials are suitable for demonstrating the spatial relationships between bones and also for the spatial relationship between bones and various devices such as tools, implants, and screws but not for simulations of procedures and processes that act upon the bone through sawing, screwing, cutting, scraping, drilling, hammering, etc. that require specific bone-related material properties such as the strength, elastic modulus, bone density (e.g., cancellous/cortical bone), heterogeneity, variability and weight etc. Current synthetic bone models use a plastic exterior and foam interior construction that, while allowing for an accurate exterior look of real bone, does not accurately simulate the feel of real bone when acted upon.

Computer simulations provide visualizations of some bone-related procedures but currently there is limited availability of such simulations and those that are available do not allow for simulation of realistic loads experienced with real instruments and procedures during bone-invasive procedures so the tactile feedback does not feel like bone. Furthermore, they do not provide the opportunity to work with real instruments in such procedures, and therefore cannot train muscle memory or true three-dimensional visual cues. Computer simulations are best used for improving knowledge rather than improving skills.

There is a growing educational trend to move away from summative training methods that evaluate overall learning across a number of learning objectives at the end of a module, towards competency-based training that evaluates specific competencies, breaking down the learning objectives into specific units. Trainees must demonstrate mastery of each competency before they are allowed to proceed to the next competency. For competencies discussed herein that are high risk and have large health and safety concerns, the competency approach has obvious advantages since it allows for progressive demonstrated skill development. However, for the procedures discussed herein there is no low risk cost-effective and reliable way to train and test such competencies before trainees perform such procedures, to refresh their skills or to demonstrate continued competency in their ongoing certification and re-certification procedures.

Similar challenges are faced within the biomechanical testing of devices that are used with bone. Currently, cadaveric models are expensive and difficult to obtain and inconsistent so are often not suitable for the control of conditions and repetition needed in biomechanical testing. Simulated bone for biomechanical testing currently consists of foam blocks that are poor proxies for real bone and only a large amount of historical use and no viable alternative has allowed these materials to be used as proxies for bone in biomechanical testing. There exists a need for improved artificial bones that perform like mammalian bone when subjected to procedures and processes that act upon the bone through sawing, screwing, cutting, scraping, drilling, hammering, etc.

SUMMARY OF THE INVENTION

This summary is provided to introduce a selection of concepts in simplified form that are further described below in the Detailed Description of Preferred Embodiments. This summary is not intended to identify key features of the claimed subject matter, nor is it intended to be used as an aid in determining the scope of the claimed subject matter.

Broadly stated, the present disclosure is directed to an artificial bone and a method of making same. Generally, a mammalian bone comprises an inner core (cancellous bone) and an outer layer (cortical bone). In accordance with one aspect of the present disclosure, a formulation and a method for making artificial cancellous bone is provided. In accordance with another aspect of the present disclosure, a formulation and a method for making artificial cortical bone is provided. In accordance with another aspect of the present invention, an artificial bone is provided comprising an inner, artificial cancellous bone core and an outer, artificial cortical bone layer. In accordance with another aspect of the present disclosure, a method for manufacturing an artificial bone is provided.

In one aspect, an artificial bone is provided, comprising a cancellous-like material made from at least one fiber component having fibers, a liquid and a binder, wherein the ratio of the fibers to fluid to binder can be varied according to a type of mammalian cancellous bone. In one embodiment, the ratio of dry fibers to liquid to binder ranges from 1:140:259 to 15:82:3. In another embodiment, the cancellous-like material is made from at least two fiber components. In one embodiment, the cancellous-like material is made from a first fiber component having primarily cellulose fibers and a second fiber component having primarily hemp fibers. In one embodiment, the liquid comprises water.

In another aspect, an artificial bone is provided, comprising a cortical-like material made from at least one fiber component having fibers, a liquid and a binder, wherein the ratio of fibers to liquid to binder can be varied according to a type of mammalian cortical bone. In one embodiment, the ratio of dry fibers to liquid to binder ranges from 1:102:97 to 12:30:158. In another embodiment, the cortical-like material is made from at least two fiber components. In one embodiment, the cortical-like material is made from a first fiber component having primarily cellulose fibers and a second fiber component having primarily hemp fibers. In one embodiment, the liquid comprises water.

In one embodiment, the artificial bone constituents are further mixed with a hardening agent such as cyanoacrylate, bone cement, epoxy, white glue (polyvinyl acetate or polyvinyl alcohol), or mineral oil (a mixture of higher alkanes from a mineral source). In one embodiment, the artificial bone further comprises a coating material to coat the artificial bone. In one embodiment, the coating material is selected from the group consisting of mineral oil, paraffin, beeswax or other natural waxes, paraffin wax blended with mineral oil, silicone blended with mineral spirits, latex paint, gum arabic, polyester resin, brown casting wax and gelatin.

In another aspect, an artificial bone is provided comprising:
an inner core made from a porous material, the porous material comprising at least one fiber component having fibers, a liquid and a binder; and
an outer layer comprising at least one fiber component having fibers, a liquid and a binder;
wherein the ratio of fibers to liquid to binder of the inner core is different from the ratio of fibers to liquid to binder of the outer layer.

In one embodiment, a coloring agent is added to the inner core or outer layer or both. In one embodiment, a different coloring agent is added to the inner core and the outer layer to differentiate between the inner core and the outer layer. In one embodiment, the coloring agent is in a powder form and is added to the inner core or outer layer or both during formulation.

BRIEF DESCRIPTION OF THE DRAWINGS

The invention will now be described by way of an exemplary embodiment with reference to the following drawings.

DETAILED DESCRIPTION OF PREFERRED EMBODIMENTS

Figure 1:
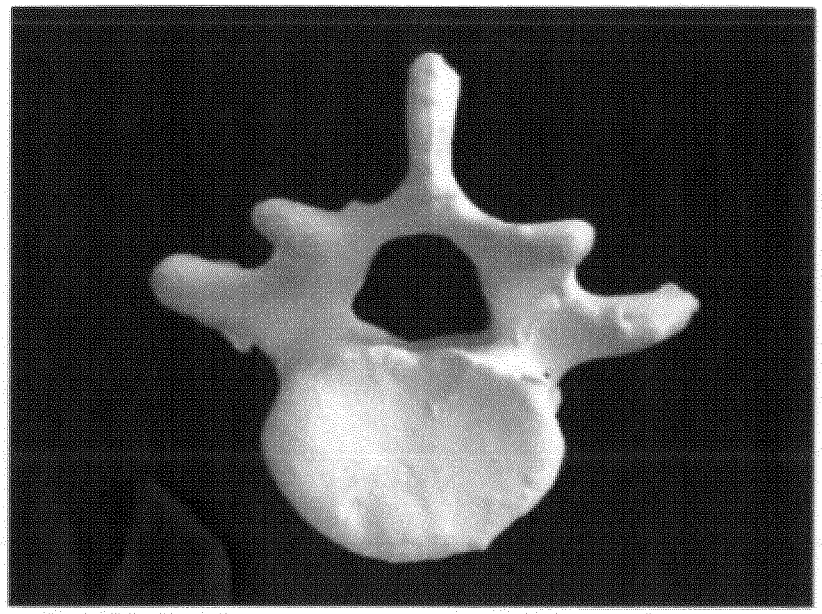
FIG. 1 is a top view of the synthetic vertebral bone analogue.

The detailed description set forth below in connection with the appended drawings is intended as a description of various embodiments of the present invention and is not intended to represent the only embodiments contemplated by the inventors. The detailed description includes specific details for the purpose of providing a comprehensive understanding of the present invention. However, it will be apparent to those skilled in the art that the present invention may be practiced without these specific details.

In this description, certain terms have the meanings provided. All other terms and phrases used in this specification have their ordinary meanings as one of skilled in the art would understand. Such ordinary meanings may be obtained by reference to technical dictionaries, such as *Hawley's Condensed Chemical Dictionary* 14$^{th}$ Edition, by R. J. Lewis, John Wiley & Sons, New York, N.Y., 2001.

As used herein, "fiber" or "fibers" means a natural or synthetic substance that is significantly longer than it is wide. As used herein, "fiber component" means a source of fiber or fibers, which fibers can be natural fibers (vegetable, wood and animal) or semi-synthetic or synthetic fibers. Fiber component may comprise vegetable fibers, which are generally based on an arrangement of cellulose and lignin, including cotton, hemp, jute, flax, ramie, sisal, bagasse and banana; wood fibers, from tree sources, which include bamboo fibers, wood shavings, bleached or unbleached kraft or sulfite pulps that are used for making paper; animal fibers such as silk and wool; semi-synthetic fibers such as nylon, Dacron and rayon; and synthetic fiber such as acrylic polyesters and Alkali Resistant Glass fibers.

As used herein, "binder" means any material or substance that help to bind fibers together to form the artificial bone. Examples of useful binders include plaster such as pottery plaster, gypsum plaster, lime plaster, or cement plaster, cement, casting plaster, bone cement and Portland cement.

As used herein, "hardening agent" means any hardening resin and the like and include cyanoacrylate, bone cement, epoxy, white glue (polyvinyl acetate or polyvinyl alcohol), or mineral oil.

As used herein, "coating material" is a material that is useful in reducing dust formation when the artificial bones of the present invention are used for biomechanical testing, surgical testing and the like, and may provide additional strength to the artificial bone. Useful coating materials may include mineral oil, paraffin wax, beeswax or other natural waxes, paraffin wax blended with mineral oil, silicone blended with mineral spirits, latex paint, gum arabic, polyester resin, brown casting wax and gelatin.

As used herein, a "coloring agent" is a natural or synthetic dye. Natural dyes are generally obtained from plant sources such as roots, berries, bark, leaves, wood, fungi and lichens. Synthetic dyes are man-made from synthetic sources such as non-living things. The dye may be added in an aqueous solution or in a powdered form. Useful coloring agents include tempera paint (primarily powder), acrylic paint, watercolor, and food dyes.

With the formulations and methods for manufacturing artificial bone material disclosed herein, one or more of the following characteristics may be realized:

a. Similar tactile feel to bone when probed, drilled, sawed, burred, fractured, gripped, hammered, or manipulated;
b. Similar cortical/cancellous thicknesses to bone with a melded boundary or with specified designs;
c. Range of mechanical properties (density/modulus/strength) possible, encompassing weak (osteoporotic), normal or strong bone or at specified levels;
d. Different geometries possible similar to the bone being simulated or with specified designs;
e. Radiodensity similar to bone or at specified levels;
f. Reduced dust production and less irritating dust compared to current synthetic bone models, i.e. more similar to bone;
g. Inhomogeneity similar to bone or at specified levels; and
h. Conductivity similar to bone or at specified levels.

Figure 3:
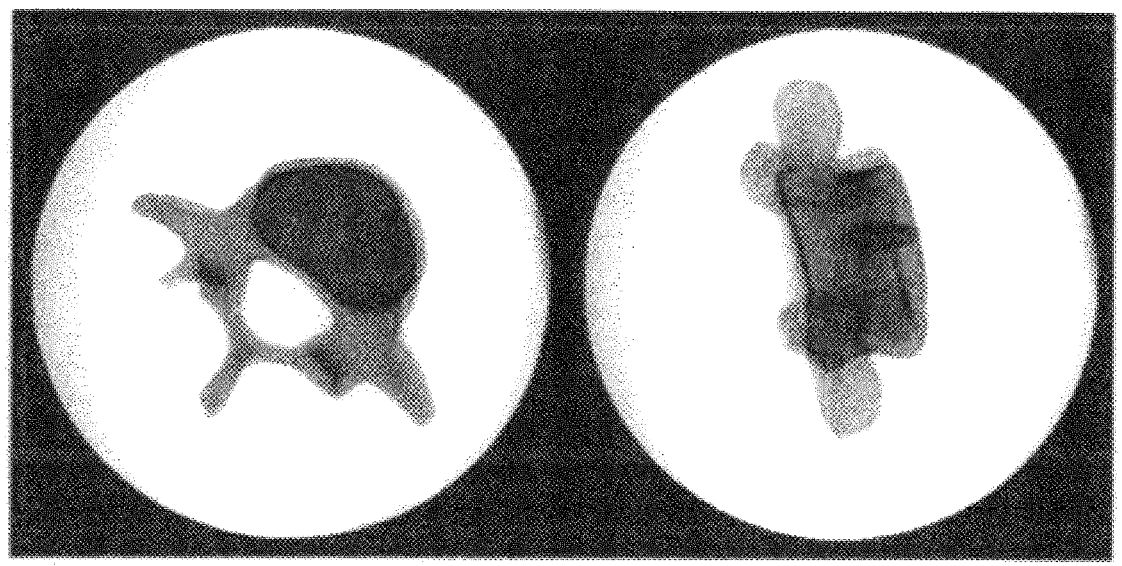
FIG. 3 shows C-arm X-ray images of the synthetic vertebral bone analogue, top and front views, showing realistic radiodensity.

In one embodiment of the present invention, a new plaster-based simulated bone is provided that provides tactile feedback that feels similar to real bone. FIG. 1 is a top view of a synthetic vertebral bone analogue manufactured according to the invention. FIG. 3 shows the X-ray images of the synthetic vertebral bone analogue of FIG. 1, top and front views, which shows the realistic radiodensity of the artificial bones of the invention.

In one embodiment, fibers of any natural or synthetic origin may be applied to the surface of or underneath the cortical layer to enhance tensile strength along the delicate features of the models including but not limited to the transverse process, spinous process, lamina, posterior vertebral arch, and/or the like.

Figure 2:
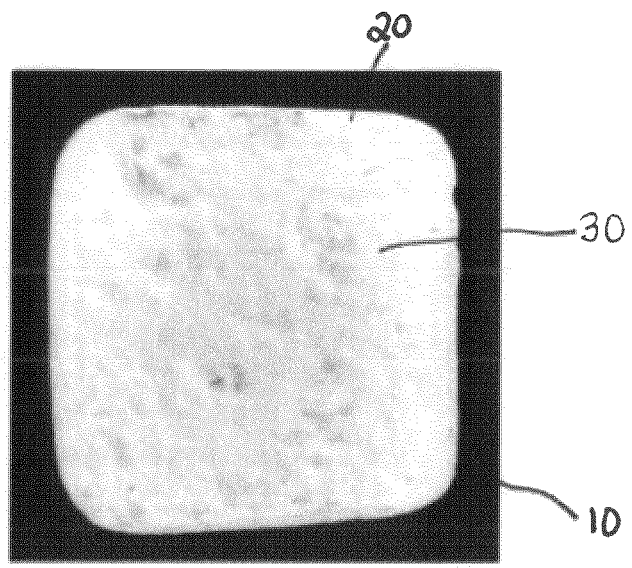
FIG. 2 is a cross-section through a cube with cancellous-like core and cortical-like (harder) outer cortex.

FIG. 2 is a cross-section through a cube 10 of the artificial bone materials of the invention. Cube 10 comprises a cancellous-like core 30 and a cortical-like outer cortex 20. Outer cortex 20 is made from a harder material than the core 30. Core 30 generally has a porous structure whereas outer cortex 20 is more rigid.

The artificial bones of the invention may be optionally combined with simulated muscle, fat, skin, ligaments and tendons to give the end-user a more realistic training system to practice on. The artificial bones of the invention may be utilized by one or more of the following end-users in human or veterinary medicine applications: medical students; medical residents (e.g., practicing pedicle screw placement and total knee arthroplasty); surgeons (e.g., navigation techniques, certification, re-certification or practicing a case preoperatively on a patient-specific generated model); dentist trainees (e.g., practicing dental drilling); engineers or technicians (e.g., conducting biomechanical testing); sales personnel (e.g., product demonstrations); educators (e.g. anatomical teaching to students and patients); and children (e.g., educational toys).

The artificial bones of the invention may include spine, femur, tibia, patella, fibula, pelvis, humerus, scapula, clavicle, ulna, radius, foot, hand, hip, knee, ankle, shoulder, wrist, leg, arm, mandible-maxilla, sacrum, skull, sternum, ribs, teeth, bone marrow, encompassing all bones and joints of the body. The artificial bones of the invention may be used for conducting one or more of the following procedures or any other bone-related procedure: pedicle screw placement, joint replacement surgery (e.g. knee, hip, and shoulder), surgical navigation techniques (e.g. for joint replacement), fracture fixation (e.g. femur, tibia, humerus, wrist, and ankle), dental drilling, arthroscopy, injection, targeting-sawing-drilling and repairing. The artificial bones of the invention may be used for conducting one or more of the following biomechanical tests or any other bone-related biomechanical testing: screw pull out, orthopaedic implant testing and orthopaedic instrument testing. The artificial bones of the invention may be used for product demonstrations that use bone models to illustrate aspects of the product.

EXAMPLE 1

In this example, a cancellous-like material is made from two fiber components, namely, paper, which comprises primarily cellulose and hemi-cellulose, and hemp, which comprises primarily cellulose. The binder used in this example is plaster.

In general, the elastic moduli for the cancellous-like materials of the present invention are in the 10s to several 100s MPa, depending upon the bone type. The elastic moduli for the materials were determined using the forces on a surgical probe instrumented with a load cell and the tactile feel of the bone verified by surgeons and residents.

A formulation based on dry weight for the cancellous-like material is given in Table 1 below. The amount (by weight) of paper and hemp used is dependent upon whether a stronger formula (for stronger bones) or a weaker formula (for weaker bones) is desirable.

TABLE 1

| Percent of Component | Strong Formula | Normal Formula | Weak Formula |
| --- | --- | --- | --- |
| Dry Paper | 3.92 | 5.00 | 5.96 |
| Dry Hemp | 1.31 | 1.25 | 0.99 |
| Water | 58.82 | 70.83 | 79.40 |
| Plaster | 35.95 | 22.92 | 13.65 |
| Total | 100.00 | 100.00 | 100.00 |

The paper used in this example is common printer paper (20 lb weight, white). The paper is reduced to smaller-size pieces prior to use to improve its blending capability. Kraft pulp can also be used to reduce the time for this step. The water used is tap water.

In this example, a second fiber component is also used, namely, dry hemp. However, it is understood that the second fiber component can be any natural or synthetic fiber source, for example, Alkali Resistant Glass fibers (ARG Chop Strand ½ inch length, 14 micron diameter, Sculpture Supply Canada). ARG fibers work well for producing heterogeneity, and could be used for pedicle probing or biomechanical testing. However, for actions that create particulate debris such as sawing, drilling, burring etc., hemp fibers and the like are preferably used to avoid any possible health concerns. Bamboo fibers, nylon, cotton, wood shavings, wool, acrylic could likewise be used. The plaster (binder) used is USG Pottery Plaster. Any plaster can be used to create the bone models.

Other heterogeneous components that may be useful for manufacturing the cancellous-like material may include one or more of the following: fabric cotton fibers, paper snowcel, nylon fibers, and the like.

The ingredients are weighed out and the paper, water, and second fiber (or other heterogeneous component) are blended in a mixer such as a blender or by hand. Alternatively, more water could be used to blend and the blended materials would then be centrifuged out to a specific weight to account for the right amount of water in the mix before adding plaster. Once the desired wetness of the fiber pulp has been achieved, a binder such as plaster is to be added to create the final mixture. Once the final mixture has been prepared, there generally is only about 6-10 minutes of work time before the plaster sets up too much to be moldable.

The final mixture is then pressed into a mold. In one embodiment, bone molds may be made of flexible material so as to allow bending of the mold to remove the wet and still fragile cancellous bone. In one embodiment, the mold can be a one-piece mold that can be peeled open. It is understood, however, that any molds can be used, even molds made from more rigid materials and may comprise any number of parts; in another embodiment, the molds are a minimum of 4 parts, and a maximum of 12. The parts of the molds fit together along easy parting lines to minimize bending needed to remove the fragile bone to reduce the likelihood of breaking it. The mold parts are held tight by a harder outer casing that can be clamped down to hold everything in place until the plaster is set. The molds are sized and shaped to specifically mimic the cancellous of a particular mammalian bone.

The final mixture is pressed into molds quickly, making sure to get into all the tight spaces. A little extra material and pressing onto the lamina will help keep them from falling apart when de-molding. If there is any "flash" around the molding pieces, it is carefully cleaned off if it seems that it will interfere with pulling molding pieces off the bone.

In general, the bone is then allowed to dry in a temperature-controlled dryer (or can be set aside to dry for about one week in the open air). It is understood that other binders could be used instead of plaster, for example, cement, gypsum, casting plaster, cyanoacrylate, bone cement, epoxy, and the like.

It is understood that the ratio of fibers to water to binder can be varied in order to customize the resultant cancellous bone to have a texture and feel that is similar to a particular species and type of real cancellous bone.

EXAMPLE 2

The cortical layer is the layer that surrounds the porous cancellous core. In general, the cortical-like layer is first manufactured as a thin slurry that absorbs into the dry cancellous-like material, creating a strongly adhered layer as the excess water is absorbed into the cancellous material. It is important for the water of the cortical slurry to absorb into the porous core to form a transition zone between the cortical-like layer and the cancellous-like core, which makes the artificial bone more like mammalian bone, i.e., less differentiation between the two components.

Generally, elastic moduli for cortical bone or layers are in the 1 to $30^+$ GPa range. Once again, the elastic moduli for the cortical layers were determined using the forces on a surgical probe instrumented with a load cell and the tactile feel of the bone verified by surgeons and residents.

In one embodiment, the thin slurry is formulated by weighing and mixing the ingredients as shown in Table 2 as follows:

TABLE 2

| Component | Weight (g) |
| --- | --- |
| Dry Paper Pulp | 1.4 |
| Water | 113.6 |
| Plaster | 110 |

This formula disperses the gypsum crystals (plaster) to create a thinner layer than the traditional mixture of water. It is understood that binders other than plaster could be used to manufacture the cortical-like layer, for example, pottery plaster, lime plaster, cement plaster, gypsum, cement, casting plaster, bone cement and Portland cement. For increased hardness of the cortical bone layers, for example, as needed for the femoral bone model, a hardening agent such as cyanoacrylate, bone cement, epoxy, white glue (polyvinyl acetate or polyvinyl alcohol), or mineral oil (a mixture of higher alkanes from a mineral source) may be added to the cortical slurry.

For bones that require thicker cortical layers, the water ratio may be changed. The ratios determined for two embodiments are in Table 3 as follows:

TABLE 3

| Femur Cortical | Weight 1 (g) | Weight 2 (g) | Percent 1 | Percent 2 |
| --- | --- | --- | --- | --- |
| Paper Pulp | 6 | 7 | 3.2 | 4.2 |
| Water | 35 | 35 | 18.8 | 21.0 |
| Glue (PVA) | 35 | 15 | 18.8 | 9.0 |
| Plaster | 110 | 110 | 59.1 | 65.9 |
| Total | 186 | 167 | 100.0 | 100.0 |

EXAMPLE 3

The cortical-like material can be added to the cancellous-like material to produce artificial bones of the invention either by dipping or by molding. In the dipping procedure, the molded cancellous-like material (e.g., the inner core) is dipped into the cortical-like material slurry, which results in a layer that thickens incrementally each time the bone is dipped. Generally, each dip of the bone should not be longer than approximately 5 seconds, as the cancellous-like material will saturate and weaken. In the molding procedure, the wet cortical-like material is put into a mold to create either a hollow or flat structure, or to have the cancellous-like material immediately or not immediately pressed therein. In one embodiment, two layers of cortical-like material are formed and the cancellous-like material is sandwiched therebetween.

In one embodiment, the cortical blend is mixed to a depth that does not allow full submersion of the bone into the blend. This is to minimize waste of cortical material, as the setting time of the plaster will be quicker than the time to use up the material, as well as prevent damage to the wet slurry as it sets up on the cancellous in approximately 5 seconds. Thus each time the bone is dipped, it must have a different orientation to ensure complete coverage of the bone. It is acceptable to pour the cortical mix over the cancellous, as well as submerge completely if able to do so.

In the molding procedure, in one embodiment, the cortical blend is placed in a mold and the cancellous core is put inside this, resulting in a consistent thickness of the cortical layer as well as control of the external geometry. In another embodiment, a cancellous core can be placed inside a cortical mold, and cortical material is injected into the mold for a consistent layer of cortical on the cancellous. In another embodiment, the cortical can be molded as a hollow structure or a single sheet and cancellous pressed onto or injected inside the structure, and layered to simulate the various bony structures in feel if not in geometry.

The time required for the plaster to set up, for example, about 6 minutes, is generally greater than the amount of time that the plaster begins to thicken, resulting in a thicker layer than desired. The pot life of the cortical blend is therefore shorter than the work-time stated on the container, and must be used or discarded sooner than that. The indication of the end of pot life is a "cottage cheese" look or overall thickening of the blend that makes the blend too viscous to flow easily.

As discussed above, the cancellous bone is generally placed in a heater for accelerated drying, before adding the cortical layer. Once the cancellous layer is sufficiently dried, the cortical layer can be added. The adhesion of the cortical layer depends on the dryness of the cancellous core. However, it has been found that even if the cancellous bone is not dried, the cortical layer can still be added. Once the cortical layer has been added, the final artificial bone will need to be dried, either in a heater for accelerated drying or for a week in the open air.

Once the bone has been allowed to sufficiently dry, a coating material may be applied such as mineral oil, paraffin wax, paraffin wax blended with mineral oil, silicone blended with mineral spirits, latex paint, brown casting wax and gelatin.

In one embodiment, a conductive element such as conductive ink, silver, metal, carbon or activated charcoal is added to either the inner core or the outer layer or both so that the inner core and/or the outer layer have different conductivities, as in real bone.

EXAMPLE 4

Tooth enamel is the hardest bone material in the human body, and the hardness of the material can be achieved by briefly soaking tooth-shaped models in certain materials. These materials may include bone cement, cyanoacrylate and epoxy. These materials are initially liquid, and may soak in appropriately without additional thinning. Should thinning be needed, however, proper solvents for the materials may be used.

EXAMPLE 5

Often when an artificial bone is being used for drilling, sawing and the like, it is desirable to reduce the dust that may be formed during these procedures. Thus, in one embodiment, once the bone model has been fully coated with cortical and allowed to fully dry, the artificial bone of the invention may be soaked in certain coatings for dust reduction and greater toughness. These coating materials may include mineral oil, paraffin wax, paraffin wax blended with mineral oil, silicone blended with mineral spirits, latex paint, brown casting wax and gelatin.

In one embodiment, the preferred coating is mineral oil. In general, these coatings must be thinned by heating (e.g. on a temperature-controlled heating plate) or by solvents in order to allow the material to soak into the bone model. The thinner the liquid, the more efficiently the liquid will soak in.

EXAMPLE 6

In some instances, it may be desirable to add a coloring agent to the cortical-like material or to the cancellous-like material or both, for aesthetic reasons, to give the artificial bone an appearance similar to bone, or to visually differentiate the cortical from the cancellous. Typically, both the cortical-like material and the cancellous-like material will include a coloring agent, for example, where the cortical is yellow and the cancellous is a yellow-brown. Preferred colors include yellow, red, and brown, sometimes in a blend but can include any other color. When using powdered tints, typically 0.25 g to 6 g of powder is added to the already outlined formulations.

Other possible tints could include anything water suspension or water miscible, natural tints could include coffee/tea, and spices like turmeric.

Although the subject matter has been described in language specific to structural features and/or methodological acts, it is to be understood that the subject matter defined in the appended claims is not necessarily limited to the specific features and acts described above. Rather, the specific features and acts described above are disclosed as example forms of implementing the claims.

While illustrative embodiments have been illustrated and defined, it will be appreciated that various changes can be made therein without departing from the spirit and scope of the disclosure.

The invention claimed is:

1. An artificial bone, comprising:
   (a) an inner core comprising a cancellous-like material made from a porous material, the porous material comprising at least one fiber component having dry fibers, a liquid and a binder; and
   (b) an outer layer comprising a cortical-like material made from at least one fiber component having dry fibers, a liquid, and a binder;
   wherein the ratio of the at least one fiber component to the liquid to the binder of the outer layer is from a range of 1:102:97 to 12:30:158 by weight,
   wherein the ratio of the at least one fiber component having dry fibers to liquid to binder of the inner core is different from the ratio of the at least one fiber component having dry fibers to liquid to binder of the outer layer,
   wherein each of the liquid of inner core and liquid of outer layer is comprised of water, and
   wherein each of the binder of inner core and binder of outer layer is selected from the group consisting of pottery plaster, gypsum plaster, lime plaster, cement plaster, casting plaster, bone cement, and Portland cement.

2. The artificial bone as claimed in claim 1, wherein the inner core comprises at least two fiber components having fibers.

3. The artificial bone as claimed in claim 1, wherein the outer layer further comprising a hardening agent.

4. The artificial bone as claimed in claim 3, wherein the hardening agent is selected from the group consisting of cyanoacrylate, bone cement, epoxy, white glue (polyvinyl acetate or polyvinyl alcohol), and mineral oil.

5. The artificial bone as claimed in claim 1, whereby the artificial bone has a similar tactile feel or similar instrument interaction forces when probing, sawing, drilling, or burring to bone.

6. The artificial bone as claimed in claim 1, wherein a conductive element such as conductive ink, silver, metal, carbon or activated charcoal is added to either the inner core or the outer layer or both so that the inner core and/or the outer layer have different conductivities.

7. The artificial bone as claimed in claim 1, further comprising adding a coloring agent to the inner core, the outer core or both.

8. The artificial bone as claimed in claim 1 further comprising: a coating material to coat the artificial bone selected from the group consisting of mineral oil, paraffin wax, beeswax or other natural waxes, paraffin wax blended with mineral oil, silicone blended with mineral spirits, latex paint, gum Arabic, polyester resin, brown casting wax and gelatin.

* * * * *